(12) United States Patent
Hadayer et al.

(10) Patent No.: US 9,921,138 B2
(45) Date of Patent: Mar. 20, 2018

(54) STERILE SAMPLE INJECTOR AND METHOD

(75) Inventors: Amir Hadayer, Beit Hashmonai (IL); Noa Hana Hadayer, Beit Hashmonai (IL); Arie Leonid Marcovich, Rehovot (IL)

(73) Assignee: Mor Research Applications Ltd., Tel Aviv (IL)

( * ) Notice: Subject to any disclaimer, the term of this patent is extended or adjusted under 35 U.S.C. 154(b) by 514 days.

(21) Appl. No.: 14/236,686

(22) PCT Filed: Aug. 6, 2012

(86) PCT No.: PCT/IL2012/000294
§ 371 (c)(1),
(2), (4) Date: Feb. 10, 2014

(87) PCT Pub. No.: WO2013/021376
PCT Pub. Date: Feb. 14, 2013

(65) Prior Publication Data
US 2014/0170644 A1    Jun. 19, 2014

Related U.S. Application Data

(60) Provisional application No. 61/515,924, filed on Aug. 7, 2011.

(51) Int. Cl.
*G01N 1/00* (2006.01)
*G01N 1/08* (2006.01)
(Continued)

(52) U.S. Cl.
CPC ............... *G01N 1/08* (2013.01); *C12M 33/04* (2013.01); *G01N 1/14* (2013.01); *G01N 35/1079* (2013.01); *G01N 2001/1427* (2013.01)

(58) Field of Classification Search
CPC ............................................. G01N 1/08
(Continued)

(56) References Cited

U.S. PATENT DOCUMENTS 4,175,008 A * 11/1979 White ............... A61B 10/0096
  206/15.2
4,418,580 A * 12/1983 Satchell ............... B01L 3/0279
  422/923

(Continued)

FOREIGN PATENT DOCUMENTS

WO    2004/003515 A2    1/2004
WO    2006066385 A1     6/2006

OTHER PUBLICATIONS

Augusto F et al: "Applications of solid-phase microextraction to chemical analysis of live biological samples", Trends in Analytical Chemistry, vol. 21, No. 6-7, Jun. 7, 2002, pp. 428-438.
(Continued)

*Primary Examiner* — Christopher Adam Hixson
*Assistant Examiner* — Emily R. Berkeley
(74) *Attorney, Agent, or Firm* — The Roy Gross Law Firm, LLC; Roy Gross

(57) ABSTRACT

A sterile injector comprises a body having a cavity, a hollow needle positionable at a distal end of the injector, a probe holder receivable within the needle, a probe connected to a distal end of the holder, and a driving element axially displaceable within the cavity, for causing relative motion between the probe and the needle upon displacement of the driving element. A sample is injected into a sealed container by displacing the driving element to a first position causing the probe to extend from the needle, applying the extended probe with a sample, displacing the driving element to a
(Continued)

second position causing the sample laden probe to be retracted within the needle, piercing a seal of a sealed container with the needle, and displacing the driving element to a third position distally spaced from the first position, after which the probe is injected into the container interior.

18 Claims, 17 Drawing Sheets

(51) Int. Cl.
*G01N 1/14* (2006.01)
*G01N 35/10* (2006.01)
*C12M 1/26* (2006.01)

(58) Field of Classification Search
USPC .......................................... 436/180
See application file for complete search history.

(56) References Cited

U.S. PATENT DOCUMENTS

| | | | |
|---|---|---|---|
| 4,772,558 A * | 9/1988 | Hammann | C12M 23/08 215/247 |
| 5,264,182 A | 11/1993 | Sakagami | |
| 5,553,508 A * | 9/1996 | Dabberdt | G01N 1/2273 73/863.02 |
| 5,691,206 A * | 11/1997 | Pawliszyn | B82Y 30/00 422/416 |
| 7,749,443 B2 * | 7/2010 | Land, III | G01N 1/405 210/634 |
| 2005/0252820 A1 * | 11/2005 | Sanchez-Felix | A61B 10/0045 206/569 |
| 2007/0166198 A1 * | 7/2007 | Sangha | A61B 10/0045 422/400 |

OTHER PUBLICATIONS

International Search Report of corresponding PCT application—dated Dec. 9, 2012, 5 pages.

* cited by examiner

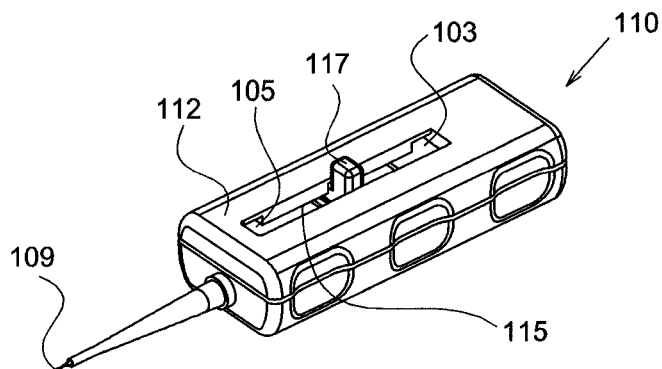
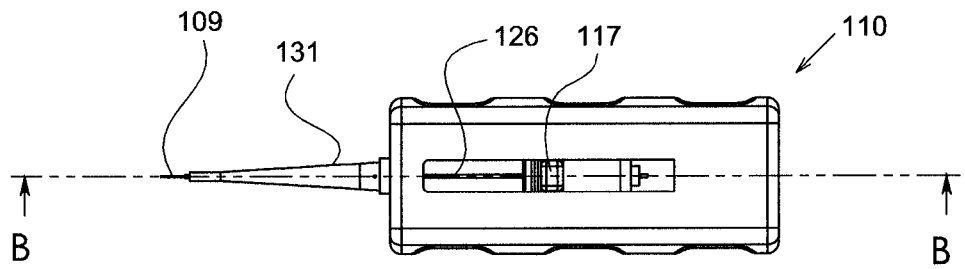
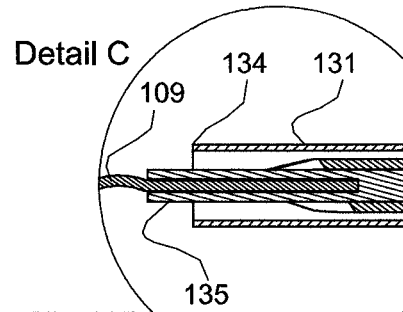
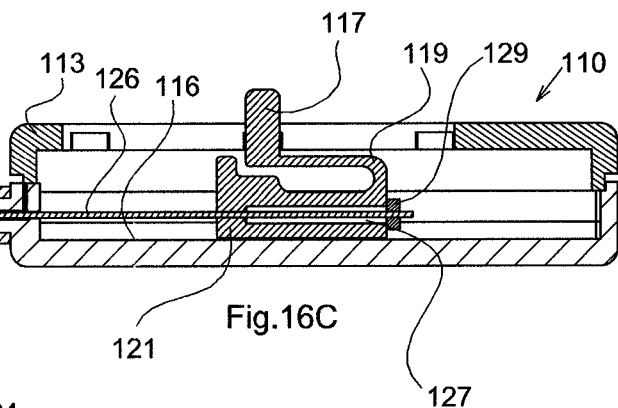
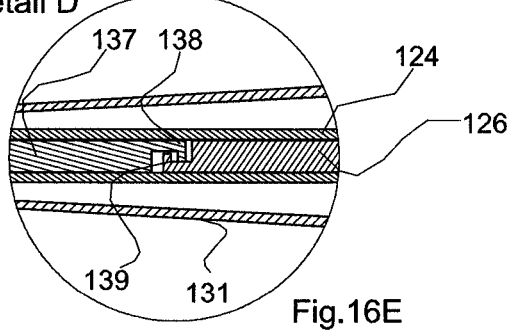

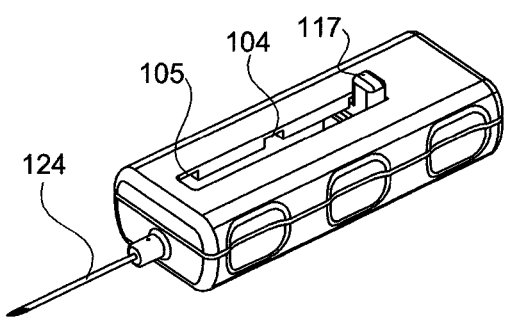
Fig. 17
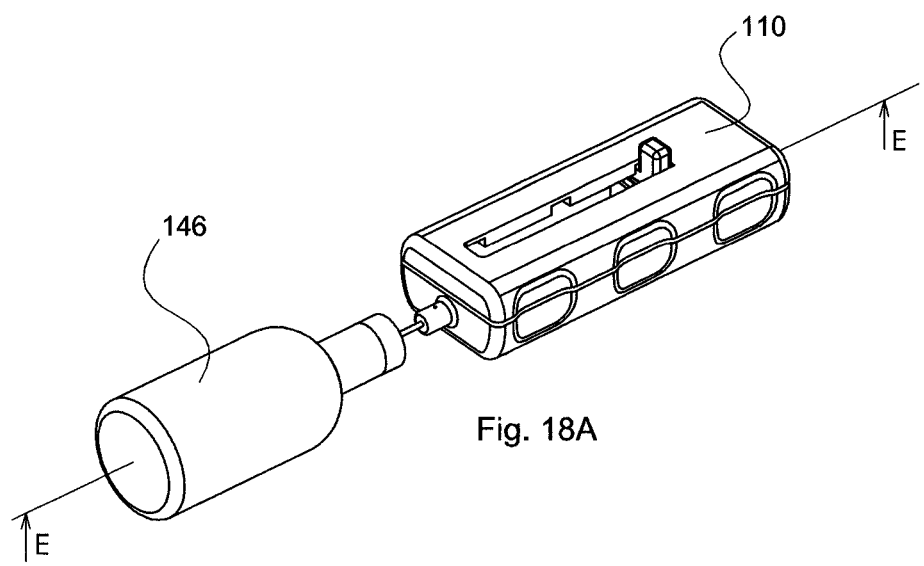
Fig. 18A
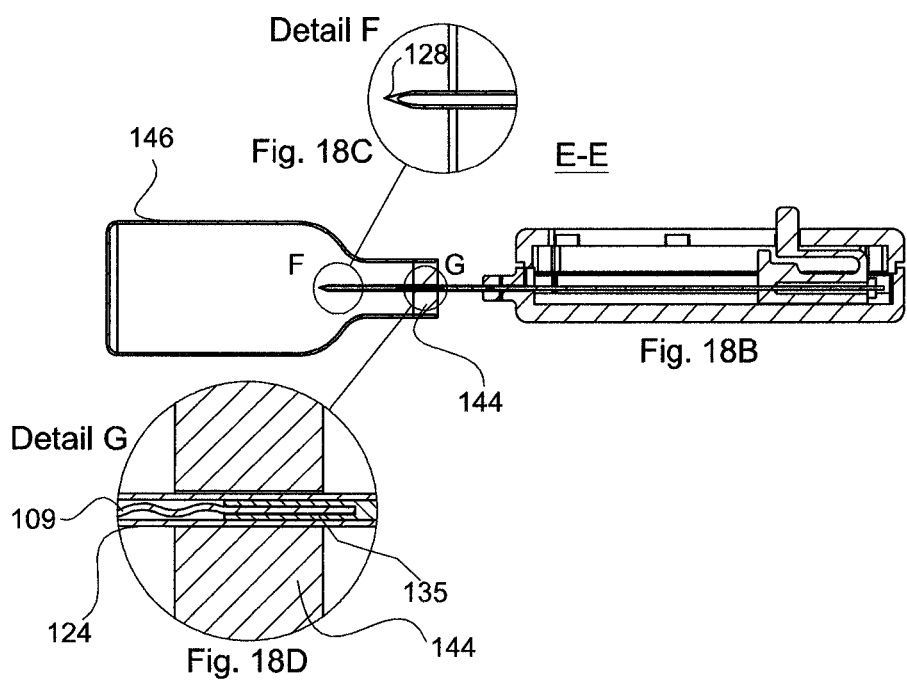
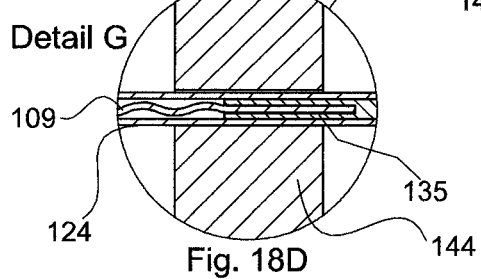

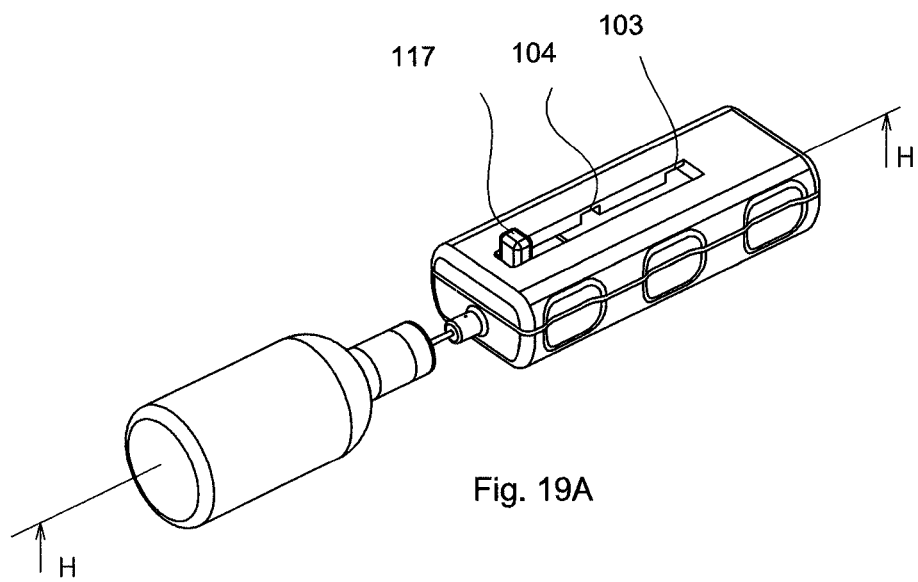
Fig. 19A
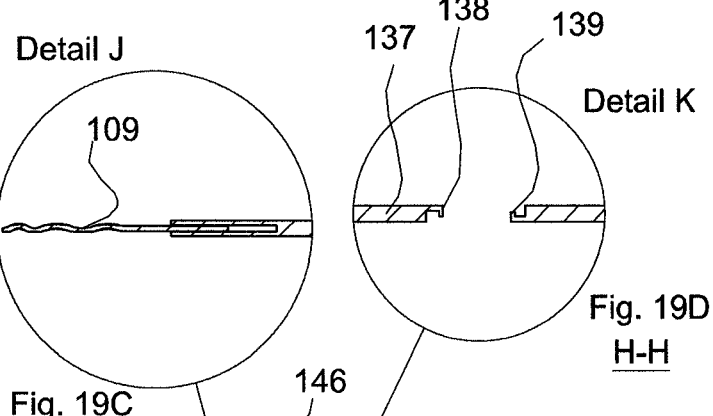
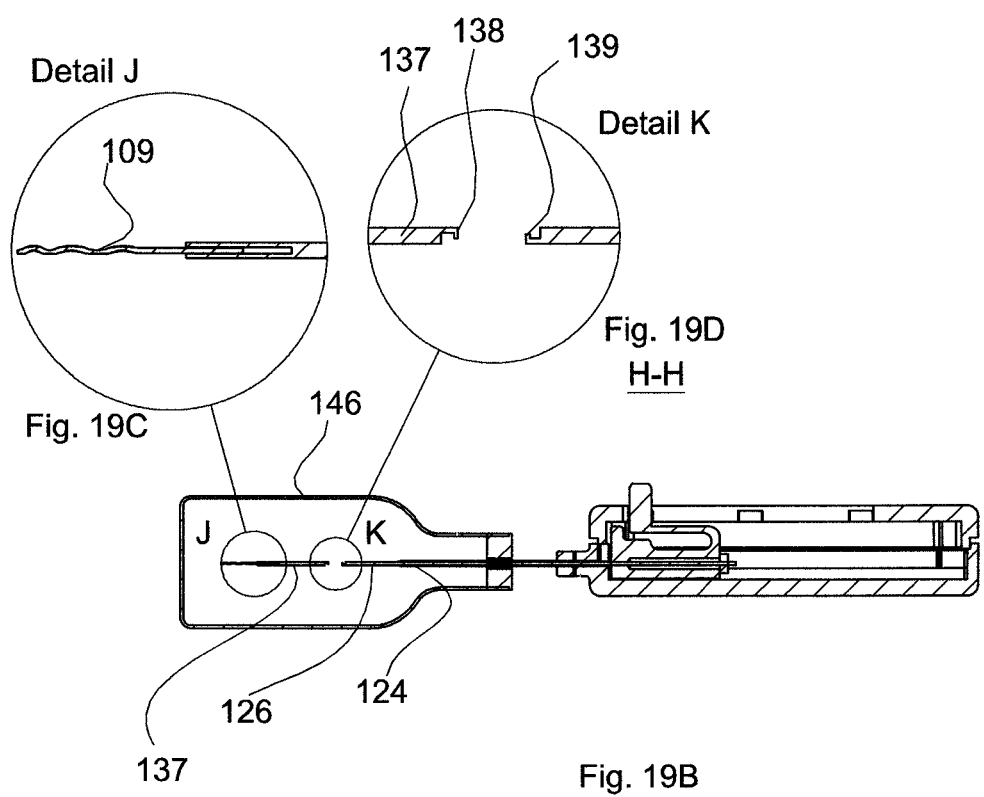
Fig. 19C
Fig. 19D H-H
Fig. 19B

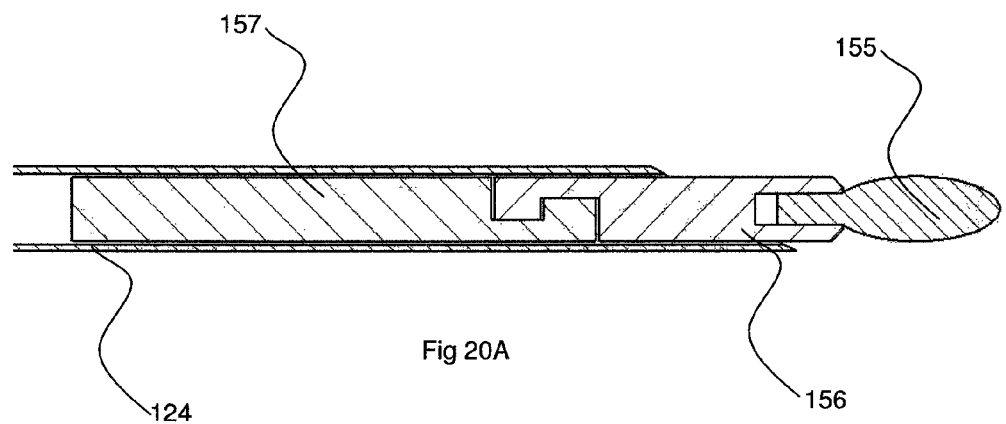
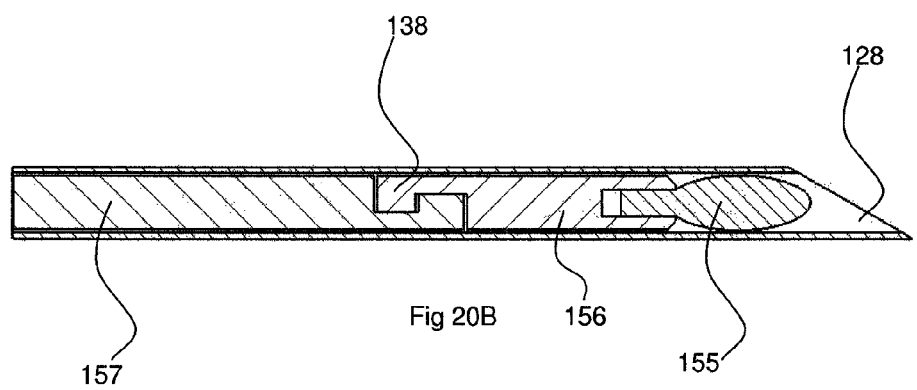
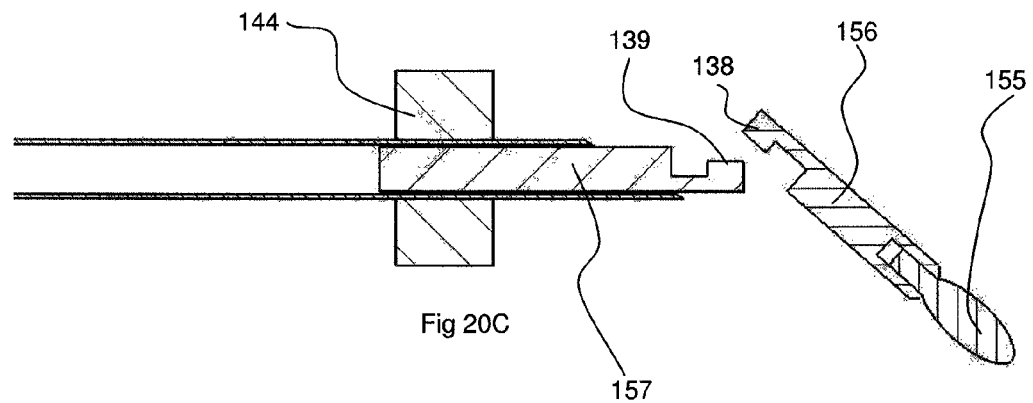

STERILE SAMPLE INJECTOR AND METHOD

REFERENCE TO CO-PENDING APPLICATIONS

Priority is claimed as a 371 of international application number PCT/IL2012/000294, filed on Aug. 6, 2012; which claims priority to U.S. provisional patent application Ser. No. 61/515,924, filed on Aug. 7, 2011.

FIELD OF THE INVENTION

The present invention relates to the field of injection devices. More particularly, the invention relates to an injector for the sterile transfer of a sample, and particularly a biological sample, to a culture bottle or any other sealed container.

BACKGROUND OF THE INVENTION

Microbiological analysis based on Petri dishes involves the seeding of a small sample within a culture medium, transfer of the Petri dish to an incubator, and a daily or tri-weekly manual inspection conducted by a bacteriologist to determine growth. Growth is generally confirmed visually as macroscopic colonies appear on the culture medium surface. This approach is laborious, necessitating technical expertise while the sample is susceptible to a relatively high risk of contamination.

Recently, sealed culture bottles which contain a culture medium including a chosen atmospheric environment and a growth indicator have been used to simplify the detection of bacterial growth. The growth indicator instantly detects biological activity such as the generation of carbon dioxide without having to wait for the appearance of macroscopic colonies. Also, antibiotic absorbing resins can be added to the culture medium to allow for the detection of bacterial growth even during antibiotic treatment. A liquid sample is injected into the culture bottle by means of a syringe without need of substantial expertise and with only a minimal risk of contamination and the culture bottle is then subjected to incubation. After being applied with a bar code, each culture bottle may be automatically sent every couple of hours to a growth analysis station by a robotic system.

Despite the widespread acceptance of the use of a culture bottle for microbiological analysis, several medical subspecialties such as ophthalmology, dermatology, otolaryngology, gynecology and surgery cannot benefit from microbiological analysis based on a culture bottle for detecting bacterial growth. With respect to these subspecialties, a culture is taken from a bodily surface, rather than from a fluid sample, and therefore cannot be readily transferred to the culture bottle without opening the seal, causing a change in the internal air pressure and gas content within the container and risking contamination.

It is an object of the present invention to provide an apparatus for transferring non-liquid bodily extracts to a culture bottle for microbiological analysis without need of opening the seal and without risking contamination of the extract.

It is an additional object of the present invention to increase the modernization of microbiological analysis by enabling the transfer of non-liquid bodily extracts to a culture bottle.

It is yet an additional object of the present invention to provide an apparatus and method for transferring non-liquid bodily extracts to a culture bottle without changing the internal air pressure and composition within the container.

Other objects and advantages of the invention will become apparent as the description proceeds.

SUMMARY OF THE INVENTION

The present invention provides a sterile injector for collecting a sample and injecting the same into a sealed container, comprising an injector body having an axially extending cavity; a hollow needle positionable at a distal end of said injector; a probe holder receivable within said hollow needle; a probe which is connected to a distal end of said probe holder; and a driving element which is axially displaceable within said cavity, for causing relative motion between said probe and said needle upon axial displacement of said driving element, wherein said probe is extendable from said needle upon a first axial displacement of said driving element in order to be applied with a sample and is retractable within said needle following a second axial displacement of said driving element in a direction opposite from said first displacement, and wherein said retracted probe is injectable into the interior of a sealed container by means of said needle following a third axial displacement of said driving element which is greater than, and in the same direction as, said first displacement.

With respect to prior art injectors having a variable chamber between an axially displaceable piston and an outlet, the only products that are easily injectable thereby are liquid products due to the difficulty in drawing non-liquid products into the variable chamber.

By virtue of the configuration of the injector of the present invention comprising a probe and probe holder which are receivable within a hollow needle, both a non-liquid and liquid sample may be applied to the probe when the latter is caused to be at least partially extended from the needle and then retained in sterile fashion within the needle after the driving element is manually actuated. Thus a non-liquid sample may be easily injected into a sealed container after the hollow needle has pierced the container seal upon subsequent axial displacement of the driving element.

As referred to herein, a "sample" is a biological sample associated with tissue from a living or formerly living entity, including humans, animals, plants, insects, bacteria, fungi, virus and any other microorganism forms, e.g. a non-liquid bodily extract, a solid bodily extract, a liquid bodily extract, or any genetic or biochemical material such as in DNA sampling, or is an inanimate entity such as a soil sample, powder, or beads, in order to be microbiologically, genetically or biochemically analyzed, a reactant material for conducting microbiological analysis such as an antibiotic binding resin, or a salt, medicament or drug, including insoluble and crystallizable powders that could not be easily injected into a sealed container without use of the injector of the present invention.

The biological sample is usable for microbiological analysis, for genetic testing, for DNA analysis, RNA analysis, protein analysis, or for any biochemical testing. The biological sample may also be a substance that is added to another sample being stored in a sealed container.

As referred to herein, the "container seal" or "seal", which is interchangeable with the term "membrane", covering the sealed container is a self sealing element e.g. made of molded thermoplastic rubber or isoprene which has sufficient elasticity so that the puncture hole formed by the penetration of the hollow needle therethrough will close after the needle is removed from the container. The "sealed container", which may be a culture bottle to enable microbiological analysis of the sample, a container provided with any genetic or biochemical material such as DNA or protein for use in DNA sampling or by research labs, a container for use in space related industries or activities, or any other receptacle, is therefore sufficiently sterile to allow the sample to be retained therewithin for a predetermined period of time without change in its microbiological or reactivity related characteristics.

In one aspect, the probe is irreversibly ejectable from the hollow needle within the interior of the sealed container upon the third axial displacement of the driving element.

In one aspect, the probe is releasably connectable to the probe holder and is detachable therefrom within the interior of the sealed container.

In one aspect, the driving element is positioned at a fully extended position following the third axial displacement.

In one aspect, the injector further comprises a manual actuator connected to the driving element for controlling the axial displacement thereof. The manual actuator may be a pin extending into a groove formed in a central peripheral portion of the injector body, said pin being guidable within said groove to define a desired axial position of the driving element.

In one aspect, the probe is made of absorbable or porous material.

In one aspect, the driving element is releasably connectable to the probe holder or to an extension thereof and is detachable therefrom within the interior of the sealed container.

In one aspect, the driving element is detachably connectable to the probe holder or to an extension thereof by means selected from the group consisting of two interengageable hook elements, a concave element in releasable engagement with a circular or spherical element, a tong member, a straight element in releasable engageable with an arcuate hook element, and a filament detachably connected to a pin.

In one aspect, each of the two interengageable hook elements comprises a thin element and a terminal element perpendicularly extending from said thin element and arranged such that the thin element of a first hook element is maintained in abutting relation with the terminal element of a second element by a wall of the hollow needle.

In one aspect, the driving element is a piston member which causes axial displacement of the probe holder by means of variable air pressure within an interior of the hollow needle.

In one aspect, the injector body is a hollow cylinder and the driving element is a piston which is axially displaceable within said cylinder, wherein one of the hollow needle and probe holder is attached to said cylinder and one of the hollow needle and probe holder is attached to said piston to cause relative motion between the probe and the needle upon axial displacement of said piston.

In one aspect, the probe holder is attached to a distal end of the piston, the hollow needle is attached to the cylinder, and the pin radially extends from the piston through the groove.

In one aspect, the hollow needle is attached to a distal end of the piston, the probe holder is attached to the cylinder, and the pin radially extends from the hollow needle through the groove.

The injector may further comprise a needle related safety device, for example a needle cover, an angled groove to prevent inadvertent axial displacement of the actuator, or a safety device releasably connectable to the driving element or to the hollow needle to prevent inadvertent axial displacement thereof.

In one aspect, the probe is releasably connectable to the probe holder and is ejectable from the hollow needle within the interior of the sealed container upon the third axial displacement of the piston. The probe may be made of compressible material and is expandable to a thickness greater than the outer diameter of the needle, causing the probe to be detached from the probe holder during contact between the expanded probe and a seal of the sealed container upon withdrawal of the needle from the sealed container.

In one aspect, a protuberance protruding from the probe holder is releasably connected to walls of a complementary cavity formed in the probe.

In one aspect, a protuberance protruding from the probe is releasably connected to walls of a complementary cavity formed in the probe holder.

In one aspect, the probe is releasably connected to the probe holder by means of two interengageable hook elements which are receivable within the hollow needle, a first hook element being attached to the probe holder and a second hook element being attached to the probe.

In one aspect, the injector further comprises an indexing turret assembly in which a plurality of probe holders are mounted, to each of said plurality of probe holders is releasably connected a corresponding probe, wherein said turret assembly is indexable following detachment of a first probe from a first probe holder so that a second probe which is uncontaminated will be made accessible to another sample.

In one aspect, the probe comprises two concave tong elements that are pivotable about a proximal common connection.

In one aspect, the probe comprises a plurality of absorbent or porous filaments.

In one aspect, the injector further comprises a needle cover which is releasably engageable with the cylinder.

The present invention is also directed to a method for injecting a sample into a sealed container, comprising the steps of axially displacing a driving element within a cavity of an injector body to a first position, thereby causing a probe disposed within a hollow needle to at least partially extend from a pointed end of said needle; applying a portion of said probe which extends from said pointed end with a sample; axially displacing said driving element to a second position, causing said sample laden probe to be retracted within said needle; piercing a seal of a sealed container with said needle; and axially displacing said driving element to a third position distally spaced from said first position, after which said sample laden probe is injected into the interior of said sealed container.

In one aspect, the driving element is connected to the probe holder or to an extension thereof by detachable connection means and is detached therefrom within the interior of the sealed container when the driving element is positioned at the third position and said connection means are completely unrestrained by a wall of the hollow needle.

In one aspect, the driving element is connected to the probe holder or to an extension thereof by a filament and the sample laden probe is irreversibly received in the sealed container upon axially displacing the driving element to a fourth position proximally spaced from the third position, causing said filament to be torn.

In one aspect, the probe is completely unrestrained by a wall of the hollow needle when the driving element is positioned at the third position. The sample laden probe consequently becomes detached from a probe holder as a result of the weakened engagement force therebetween and of the contact between the probe and the seal when the needle is being withdrawn from a puncture hole formed within said seal. The sample laden probe therefore remains within the sealed container interior.

The composition or pressure of a fluid contained within the interior of the sealed container, e.g. air, is preferably unchanged after injection therewithin of the sample laden probe. The sample is selected from the group consisting of fluid, solid, powder beads, a genetic sample for DNA, RNA or protein analysis, and a microbiological sample, and is transferred from the injector body to the interior of the sealed container in a sterile manner.

In one aspect, the sample is a biological sample, and is collected invasively or non-invasively from a bodily surface.

BRIEF DESCRIPTION OF THE DRAWINGS

In the drawings:

FIG. 16A is a perspective view of an injector according to another embodiment of the invention, wherein FIG. 16B is a plan view thereof, FIG. 16C is a cross sectional view thereof cut along plane B-B of FIG. 16B, FIG. 16D is an enlargement of Detail C, and FIG. 16E is an enlargement of Detail D;

FIG. 17 is a perspective view of the injector of FIG. 16A, showing an exposed needle while the actuator set to a retract position;

FIG. 18A is a perspective view of the injector of FIG. 16A after the needle has pierced the membrane of a sealed container, wherein FIG. 18B is a cross sectional view cut along plane E-E of FIG. 18A, FIG. 18C is an enlargement of Detail F, and FIG. 18D is an enlargement of Detail G;

FIG. 19A is a perspective view of the injector of FIG. 16A after the needle has pierced the membrane of a sealed container while the actuator set to an eject position, wherein FIG. 19B is a cross sectional view cut along plane H-H of FIG. 19A, FIG. 19C is an enlargement of Detail J, and FIG. 19D is an enlargement of Detail K;

FIGS. 20A-C are cross sectional views of an embodiment of probe releasing means, shown in three different axial positions, respectively;

DETAILED DESCRIPTION OF PREFERRED EMBODIMENTS

Prior art syringe-type injectors allow liquids to be transferred and injected but are unable to reliably transfer non-liquid samples, e.g. for use in microbiological studies. The inability of non-liquid samples to be transferred into a sealed container can be attributed to many factors including, without being bound to any theory, the lack of plasticity of many non-liquid materials that would be needed to induce flowability during air assisted injection, poor sealing and usually increased contamination when a solid sample is desired to be injected since the sealing elements is provided with a standard configuration and will usually not sealingly engage the solid sample, the coalescency of powder samples that would resist flowability during injection, and the increased subatmospheric pressure that needs to be generated in order to draw the sample into the injector.

The novel injector of the present invention employs an extendable and retractable probe for absorbing a sample and retaining it without contamination prior to being transferred to a culture bottle or any other sealed container.

Figure 1:
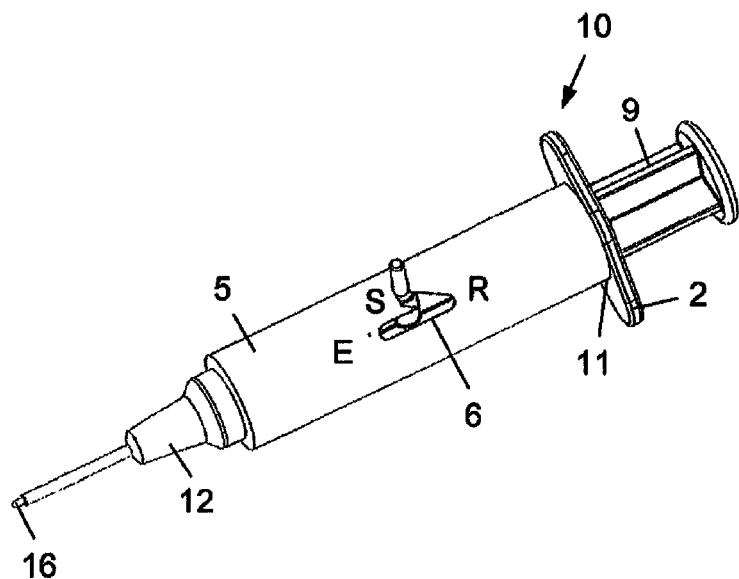
FIG. 1 is a perspective view of a sterile sample injector, according to one embodiment of the present invention, showing a probe protruding from a needle cover.
Figure 2:
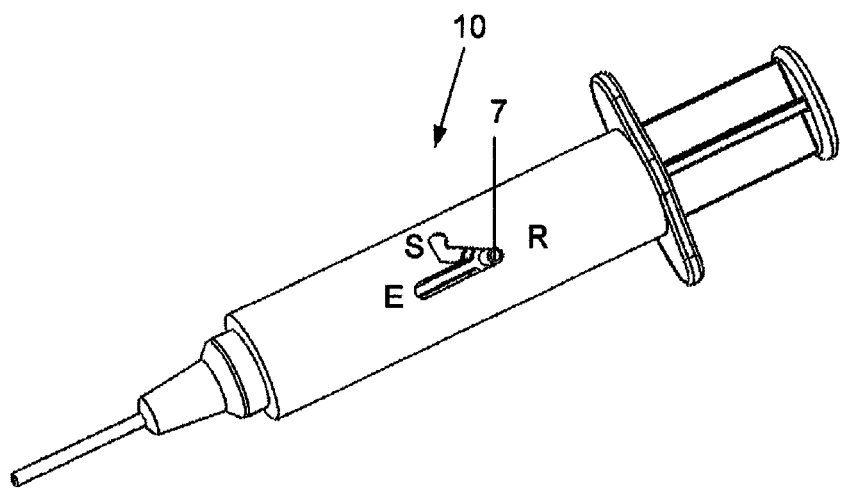
FIG. 2 is a perspective view of the injector of FIG. 1, shown after the probe has been retracted.

FIGS. 1 and 2 illustrate a sterile sample injector generally designated by numeral 10, according to one embodiment of the present invention. Injector 10 comprises a hollow cylinder 5 formed with an angled groove 6 in a central portion of its periphery, a piston 9, e.g. an elongated piston such as a plunger, that is axially displaceable by a tight fit within cylinder 5 and from which radially protrudes a mode selector actuator pin 7 guidable within groove 6, a cover 12 for covering a hollow needle attached to cylinder 5, and a probe 16 that is selectively extendable from, and retractable into the hollow needle. An annular finger gripping flange 2 is attached to the proximal end 11 of cylinder 5 and radially extends therefrom.

Probe 16 made of an absorbent or porous material, which also may be a compressible material, is shown to be protruding from needle cover 12 in FIG. 1 when actuator pin 7 is set to a start position S, and is retracted when actuator pin 7 is set to a retract position R, as shown in FIG. 2.

Figure 3:
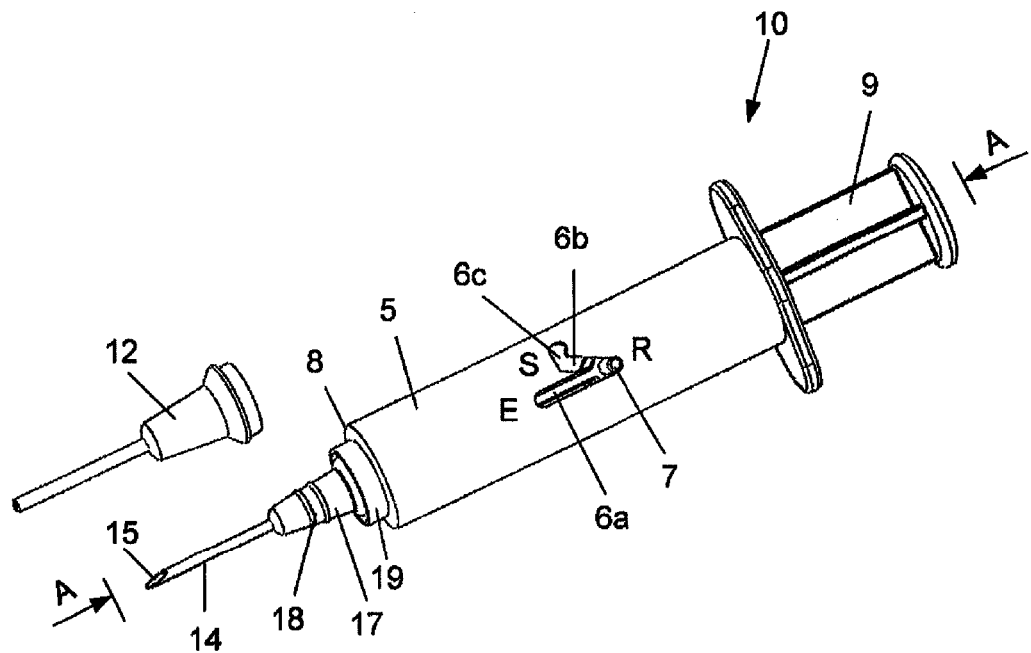
FIG. 3 is a perspective view of the injector shown in the position of FIG. 2 after the needle cover has been removed.

FIG. 3 illustrates injector 10 when the disposable needle cover 12 is removed, exposing a distally disposed hollow needle 14 with a pointed end 15.

Proximally extending from hollow needle 14 is a hollow frusto-conical abutment element 17, the diameter of which is larger than needle 14 and which gradually increases in a proximal direction. Two axially separated circumferentially extending elements 18 protrude from the periphery of abutment element 17. A hollow coupling element 19 of circular cross section protrudes from the distal flat end 8 of cylinder 5. Needle cover 12 is shaped similarly to the configuration of needle 14, abutment element 17 and coupling element 19.

The groove formed in the periphery of cylinder 5 has an axially extending portion 6a which extends from a retract position R to an eject position E, an oblique portion distally extending from retract position R, and a transverse portion 6c extending from one end of oblique portion 6b to start position S located between retract position R and eject position E. When actuator pin 7 is guided to one of the positions S, R or E, piston 9 is caused to be correspondingly displaced axially in order to control movement of the probe, as will be described hereinafter.

Figure 4:
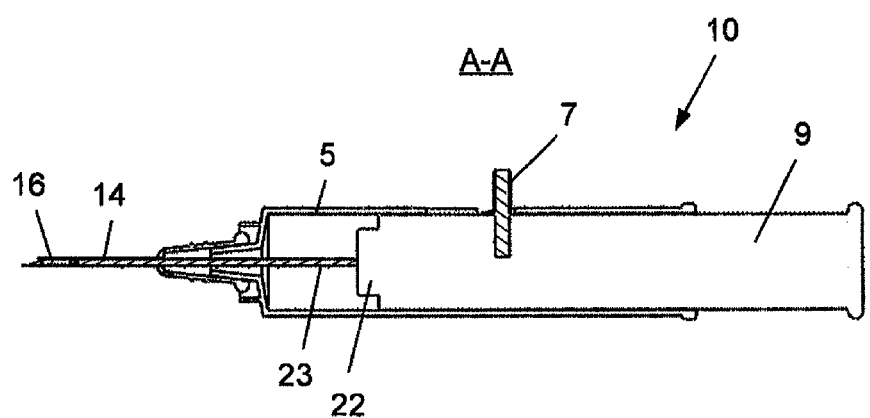
FIG. 4 is a cross sectional view of the injector of FIG. 1, cut along plane A-A of FIG. 3.

FIG. 4 illustrates a cross sectional view of injector 10. As shown, a solid cylindrical probe holder 23 distally extends from a distal shoulder 22 formed in piston 9. Probe holder 23, which also may be hollow, is adapted to be received within the interior of needle 14 and to cause probe 16 to be axially displaced.

Figure 5:
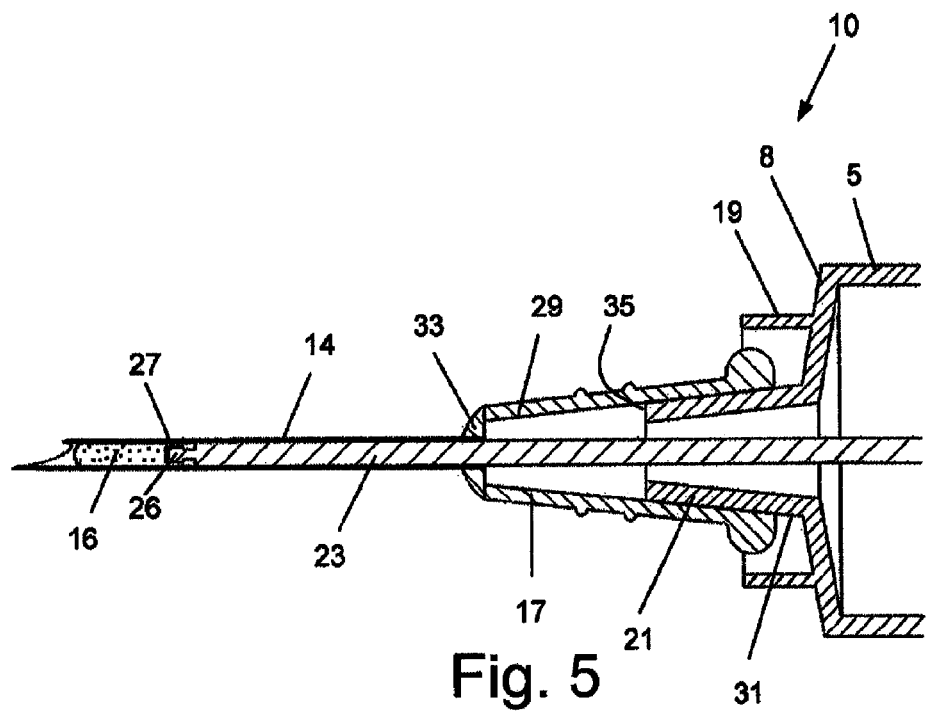
FIG. 5 is an enlargement of FIG. 4, showing the distal end of the injector of FIG. 1 while the probe is in a retracted position.

FIG. 5 is an enlargement of FIG. 4, showing the distal end of injector 10. Probe holder 23 has a protuberance 26 that protrudes from its distal end, or is connected thereto by a throat element, for connection with complementary rigid walls of a cavity 27 formed in probe 16. When in a retracted position as shown, probe 16 is compressed and received within the interior of needle 14 Probe 16 is shown to have a semi-elliptical shape; however, it may assume other shapes as well.

A hollow mounting element 21 having an inwardly sloping wall with a circular cross section extends distally from a central region of distal end 8 of cylinder 5. The inner surface 29 of abutment element 17 is adapted to contact, and to be attached to, the outer surface 31 of mounting element 21 by any suitable attachment means well known to those skilled in the art, including threaded attachment and adhesion. An interface element 33 at the distal end of abutment element 17 is connected to, or integrally formed with, the proximal end of needle 14, and is axially spaced from the distal end 35 of mounting element 21 due to the slope of abutment element 17 and mounting element 21.

Figure 6:
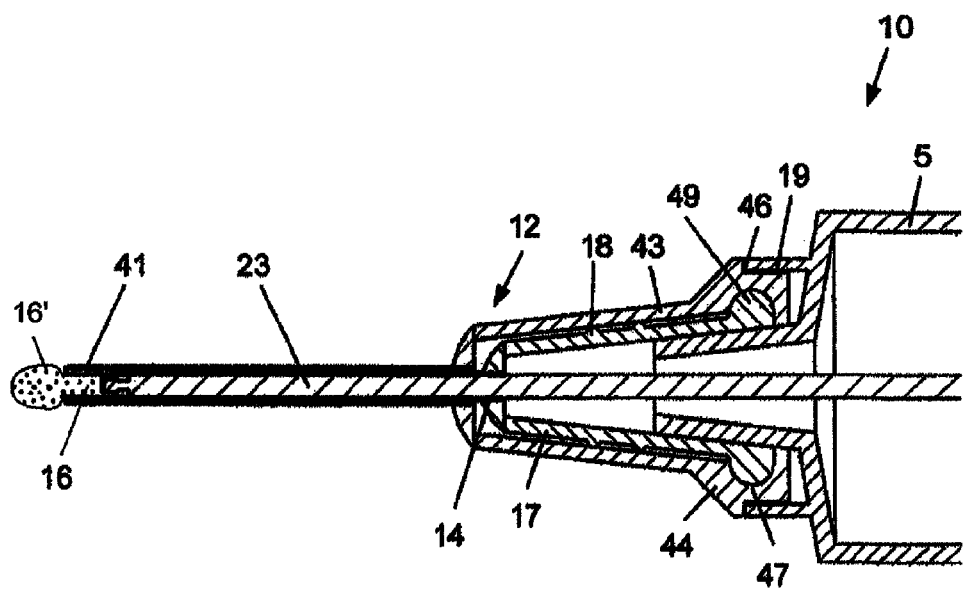
FIG. 6 is an enlargement of FIG. 4, showing the distal end of the injector of FIG. 1 to which is coupled the needle cover while the probe is in an extended position.

FIG. 6 is similar to FIG. 4, but with the addition of needle cover 12, shown while a compressible and expandable probe 16 is in a partially extended position. The portion 16' of probe 16 distally extending from needle cover 12 is shown to expand to a larger size since it is no longer constricted by the wall of hollow needle 14.

Needle cover 12 comprises elongated element 41 adapted to surround needle 14 and to prevent injury as a result of contact with its pointed end, an abutment element enclosure 43, and a thickened portion 44 for engagement with coupling element 19 of cylinder 5, which may be formed with a circumferential recessed shoulder 46. Thickened portion 44 may also be formed with a concave recess 47 for engagement with a convex protrusion 49 at the proximal end of abutment element 17. Abutment element 17 is preferably made of flexible material such as rubber to facilitate engagement with convex protrusion 49. Circumferentially extending elements 18 increase the frictional contact between abutment element 17 and enclosure 43 of cover 12.

In operation, actuator pin 7 is first set to start position S while needle cover 12 is engaged to abutment element 17, as shown in FIGS. 1 and 6. Piston 9 and probe holder 23 connected thereto are thereby caused to be distally displaced to an intermediate position, causing in turn probe 16 which is connected to probe holder 23 to be partially extended from needle cover 12. A sample is then transferred to probe 16 in a first step. The sample is preferably a biological sample from a bodily surface, including but not limited to non-liquid bodily extracts associated with the conjunctiva, cornea, skin, nails, vagina, cervix, uterus, auditory canal, nasal mucosa, and infected wounds, or liquid bodily extracts such as sputum and tears, which can therefore be easily non-invasively transferred to probe 16; however, other types of samples are also in the scope of the invention.

In a second step for transferring a sample, actuator pin 7 is set to retract position R, and the probe is caused to be retracted into the hollow needle, as shown in FIG. 2. Accordingly, contamination of the sample is prevented as it is protected within the interior of the needle.

Figure 7:
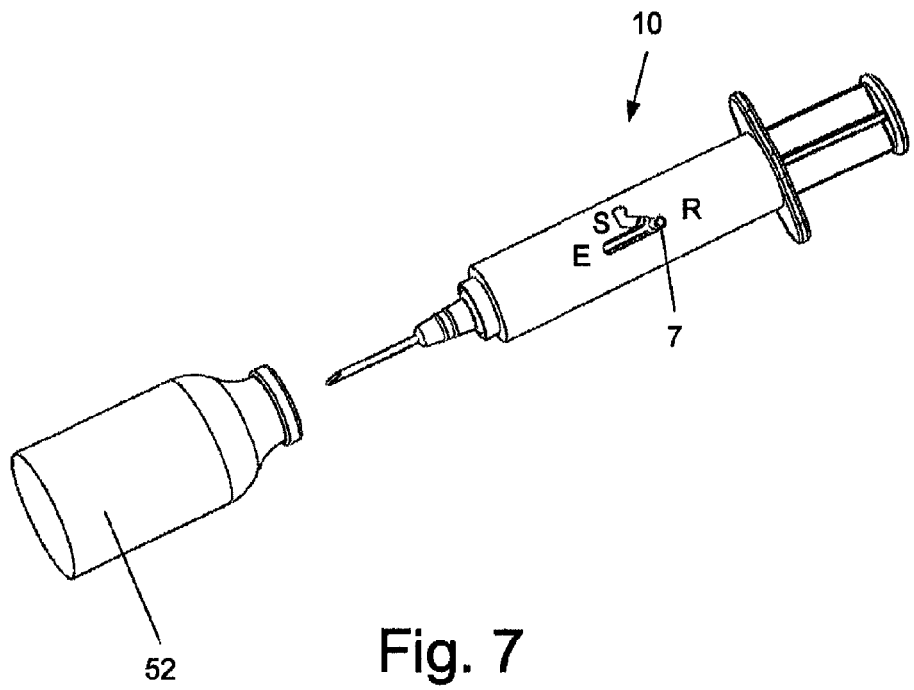
FIG. 7 is a perspective view of the injector of FIG. 1, shown in preparation of transfer of a sample to a culture bottle.
Figure 8:
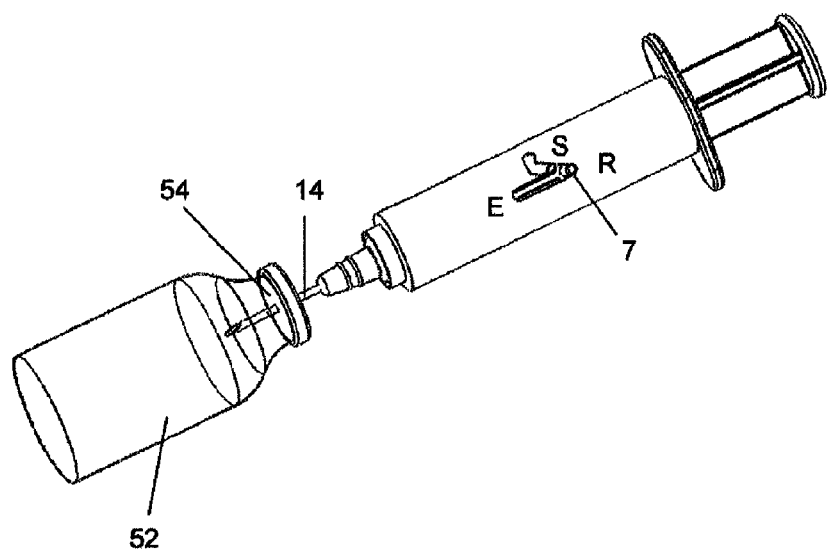
FIG. 8 is a perspective view of the injector of FIG. 1, shown after its needle has pierced the membrane of a culture bottle.

While actuator pin 7 remains at retract position R, the needle cover is then removed from injector 10 in preparation of transfer of the sample to culture bottle 52, as shown in FIG. 7. Needle 14 is then caused to pierce and penetrate rubber membrane 54 of culture bottle 52 while being introduced into the culture bottle interior, as shown in FIG. 8.

Figure 9:
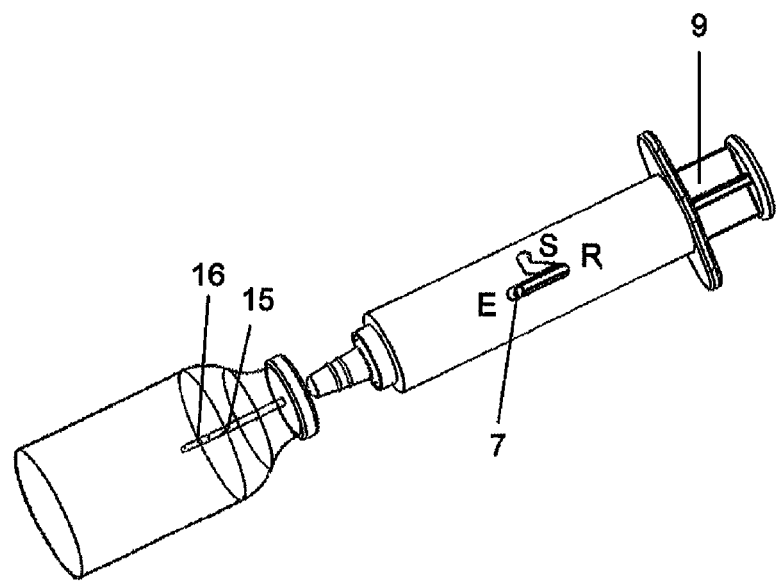
FIG. 9 is a perspective view of the injector of FIG. 1, showing the probe being extended completely beyond the pointed end of the needle within the culture bottle while continuing to be connected to the probe holder.

In a third step shown in FIG. 9, actuator pin 7 is set to eject position E and piston 9 is distally displaced to a fullest extent such that protuberance 26 of probe holder 23 (FIG. 5) is positioned distally from pointed end 15 of the needle. Since probe 16 is no longer restrained by the inner wall of the needle, it is free to expand to a thickness that is greater than the outer diameter of the needle. At this extreme distal position of probe 16, the engagement force between protuberance 26 of probe holder 23 and rigid cavity walls 27 of probe 16 becomes weakened.

Figure 10:
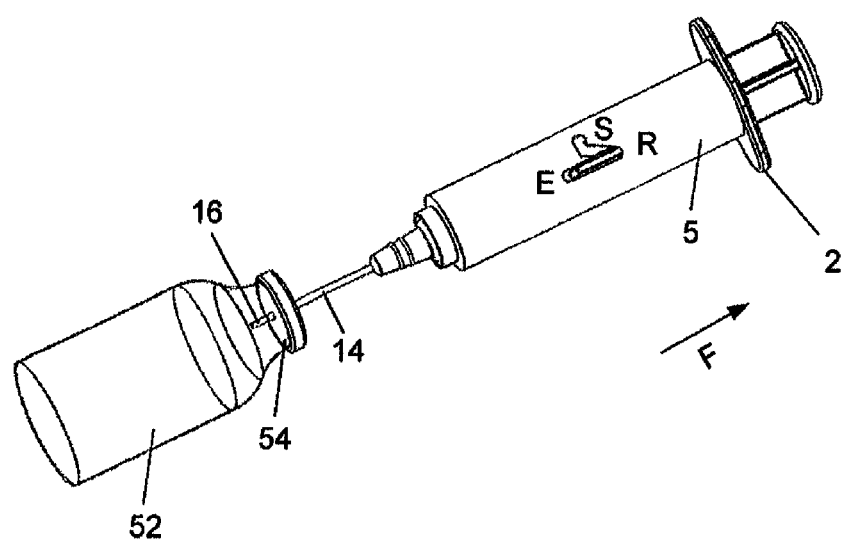
FIG. 10 is a perspective view of the injector of FIG. 1, showing the probe being detached from the probe holder.
Figure 11:
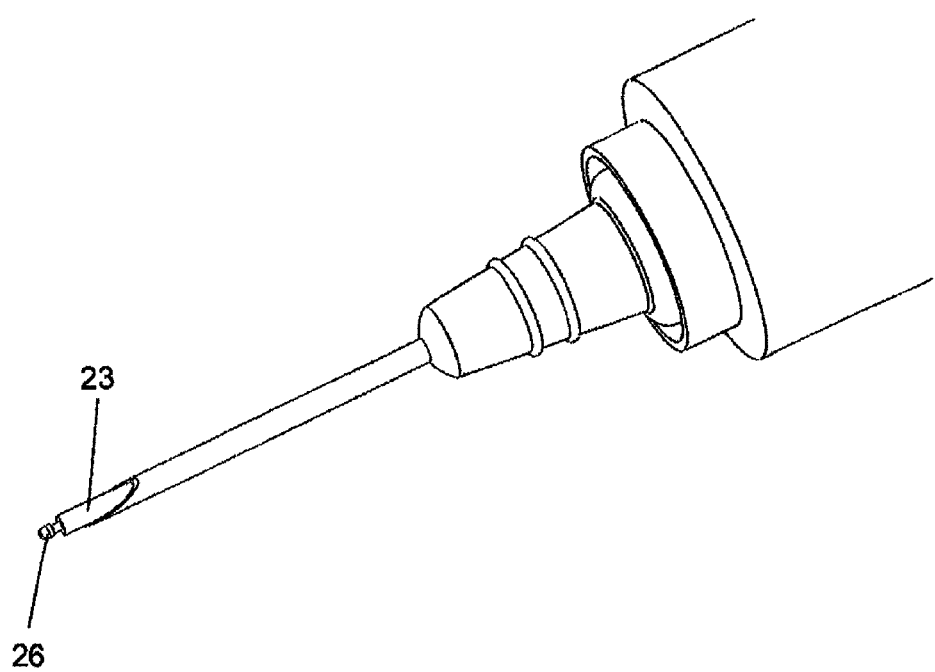
FIG. 11 is a perspective view of the distal end of the injector of FIG. 1, showing its probe holder after the probe has been detached therefrom.

In a fourth step shown in FIG. 10, a proximally directed force F is applied to flange 2 of cylinder 5, allowing needle 14 to be withdrawn from culture bottle 52 via the puncture hole made in membrane 54. Probe 16, however, is unable to be withdrawn through the puncture hole after having been expanded to a thickness greater than the outer diameter of needle 14. Due to the contact between the expanded probe and membrane 54, the probe is caused to be detached from the probe holder. FIG. 11 illustrates protuberance 26 of probe holder 23 after having been separated from the probe.

Figure 12:
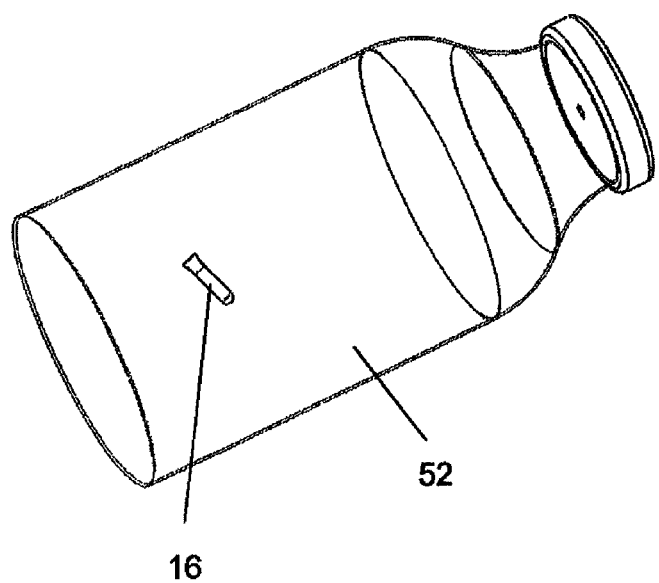
FIG. 12 is a perspective view of a culture bottle, showing a probe being retained therewithin.

The detached probe 16 therefore remains in culture bottle 52, as shown in FIG. 12, allowing microorganisms to be detected in the collected sample even during an antibiotic treatment. The membrane of culture bottle 52 is self sealing. Thus the puncture hole caused by the needle becomes closed upon removal of the needle, ensuring that the collected sample will remain in a sterile environment, without any change in the pressure or composition of the air contained within the interior of the culture bottle.

Figure 13:
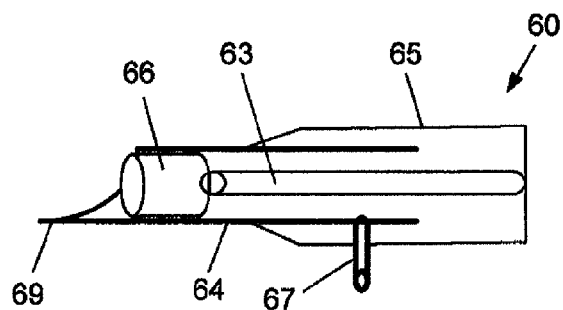
FIG. 13 is a schematic illustration of a portion of a sample injector according to another embodiment of the invention.

In another embodiment of the invention schematically illustrated in FIG. 13, the probe is stationary and the hollow needle is axially displaceable with respect to the probe.

Injector 60 comprises a probe holder 63 that is fixed to cylinder 65 and releasably connected to probe 66. Probe 66 is received within the interior of hollow needle 64. Elongated hollow needle 64 is positioned by a tight fit within cylinder 65, while allowing relative axial motion relative to the same by means of mode selector actuator pin 67, which is radially connected to the piston, or any other driving element Mode selector actuator pin 67 radially protrudes from the periphery of hollow needle 64, and is guidable within an angled groove formed within the periphery of cylinder 65. Actuator pin 67 is set to a different position during each step for transferring a sample by means of injector 60, causing relative axial motion between hollow needle 64 and probe 66. Axial displacement of hollow needle 64 therefore causes probe 66 to be positioned distally with respect to pointed end 69 of needle 64, in order to be applied with a sample or to be detached from probe holder 63 within the culture bottle. When it is desired to cause probe 66 to be detached from probe holder 63, needle 64 is proximally displaced to a fullest extent and the probe is caused to contact the culture bottle membrane.

Injector 60 may also comprise a safety device well known to those skilled in the art to prevent inadvertent axial displacement of hollow needle 64.

Figure 14:
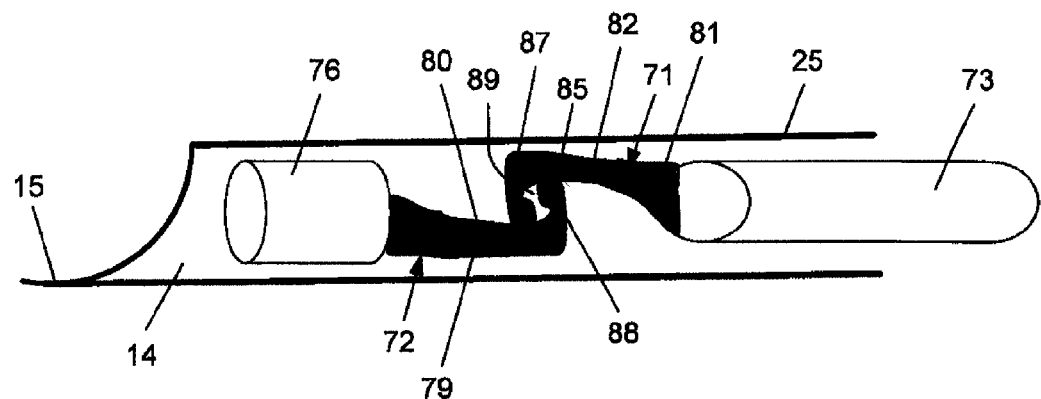
FIG. 14 is a schematic illustration of two interengageable hook elements by which a probe is releasably attachable to a probe holder.

FIG. 14 illustrates another arrangement for causing the probe to be detached from the injector. Two flexible, interengageable hook elements 71 and 72 adapted to be received within hollow needle 14 are used for releasably engaging probe 76 to probe holder 73.

Each hook element comprises a thickened connecting portion 81, a relatively thin central portion 82 axially extending from connecting portion 81, and a trapezoidal terminal portion 85 which is laterally and axially spaced from central portion 82. A thickened abutment portion 87 is formed at the end of central portion 82, and a substantially planar surface 88 at the axial end of the hook element laterally extends from abutment portion 87 to terminal portion 85. While an outwardly facing surface 79 of the hook element is substantially straight, an inwardly facing surface 80 thereof is concave and serves as a camming surface with which terminal portion 85 of the other hook element is frictionally engageable. Inwardly facing concave surface 80 extends from connecting portion 81 to the outward end of terminal portion 85 to define a seat 89 for engaging the terminal portion of the other hook element.

Connecting portion 81 of hook element 71 is attached to the distal end of probe holder 73 and connecting portion 81 of hook element 72 is attached to the proximal end of probe 76. Thus when the piston to which probe holder 73 is attached is proximally displaced, the two hook elements 71 and 72 become interengaged when each terminal portion 85 becomes engaged with the seat 89 of the other hook element, causing probe 76 to be also proximally displaced.

When probe holder 73 is distally displaced, the two terminal portions 85 become separated as shown. Due to the frictional engagement of terminal portion 85 of hook element 71 with concave surface 80 of hook element 72, the distal displacement of probe holder 73 causes probe 76 to be distally displaced as well. Despite the frictional engagement between terminal portion 85 of hook element 71 with concave surface 80 of hook element 72, terminal portion 85 of hook element 71 is displaced along concave surface 80 of hook element 72 while being increasingly spaced from terminal portion 85 of hook element 72. Abutment portion 87 of hook element 71 is consequently caused to be vertically displaced as a result of the contact of the corresponding terminal portion with upwardly sloping surface 80 of hook element 72. The vertical displacement of abutment portion 87 of hook element 71, as well as that of abutment portion 87 of hook element 72 caused by the proximal displacement of terminal portion 85 of hook element 72 along concave surface 80 of hook element 71, is limited when contacting the inner surface of needle wall 25.

When probe holder 73 is distally displaced to a fullest extent after needle 14 has been injected into the culture bottle, the abutment portion of hook elements 71 and 72 cease to be confined by needle wall 25. The terminal portions of hook elements 71 and 72 are therefore sufficiently separated to cause probe 76 to be disengaged from probe holder 73.

Other arrangements for causing the probe to be detached from the injector are also in the scope of the invention. For example, the probe may be adhesively attached to the probe holder by a weak bond which is easily detachable when the probe contacts the culture bottle membrane or seal when the hollow needle is being removed from the culture bottle.

It will be appreciated that other types of probes may be employed, for example one comprising a plurality of filaments, each of which is made of absorbent or porous material for absorbing the sample, e.g. a biological sample.

Figure 15:
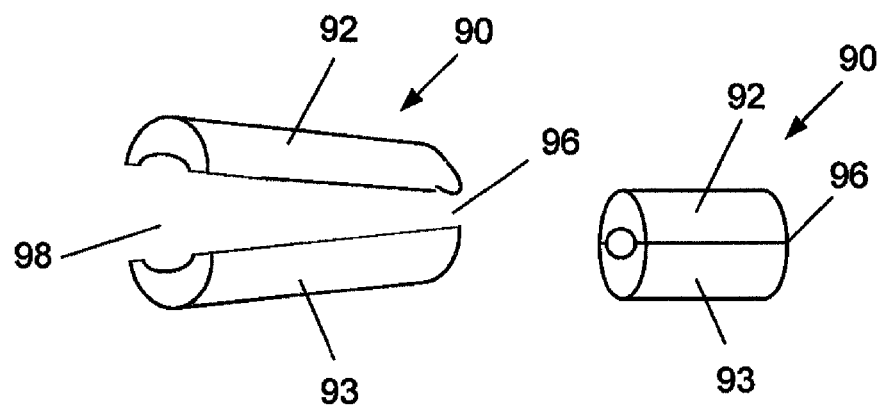
FIG. 15 is a perspective view of a tong-like probe, shown in an open and closed position.

FIG. 15 illustrates a tong-like probe 90, which comprises two concave tong elements 92 and 93 that are pivotable about a proximal common connection 96. An applicator collects the sample and transfers the same to within the interior 98 of probe 90 between tong elements 92 and 93. This probe is particularly suitable for receiving solid samples, such as tissue from a corneal abscess or a soil or mineral sample, or viscous samples such as pus, and is detachable from the probe holder by any means described herein.

FIGS. 16-19 illustrate another embodiment of the invention wherein injector 110 has a rectilinear body 112 in which a linearly extending groove 115 for guiding actuator 117 is formed.

As shown in FIG. 16C, actuator 117 is connected, e.g. by means of arcuate element 119, to block 121, which is in abutting and slidable relation with bottom 116 of groove 115. An elongated wire 126 is received in cavity 127 formed in block 121, and is secured to block 121 by means of fastening element 129, e.g. a nut with which wire 126 is threadedly engaged. Wire 126 distally extends into the interior of hollow needle 124 shown in FIG. 16E, which is connected such as by threaded engagement to the distal end 113 of the injector body and initially enclosed by needle protector 131.

With reference to FIGS. 16A-E, the probe for this embodiment is an absorbable filament 109, e.g. a thread. Filament 109 is positioned at a selected axial distance from the tip 134 of needle protector 131 by means of annular probe holder 135 in which filament 109 is received and secured, and probe holder 135 in turn is secured to elongated probe holder extension 137. Extension 137 is releasably attached to wire 126 by means of two interengageable hook elements 138 and 139, each of which having a thin element and a terminal element perpendicularly extending from the thin element and arranged such that the thin element of a first hook element is maintained in abutting relation with the terminal element of a second element by the wall of hollow needle 124.

Groove 115 is provided with three axially separated seats 103, 104 and 105, in each of which actuator 117 is receivable, in order to select a different mode of operation. Actuator 117 is received in seat 104 when displaced to an intermediate position, causing filament 109 to be extended outwardly from needle protector 131. When actuator 117 is received in seat 103 as shown in FIG. 17, filament 109 is completely retracted into the interior of hollow needle 124 while exposing the tip of needle 128. After needle protector 131 is removed, needle tip 128 is then caused to pierce membrane 144 of container 146, e.g. a culture bottle, as shown in FIGS. 18A-D, while the axial position of probe holder 135 or filament 109 within the interior of needle 124 coincides with the membrane, depending on the length of wire 126 and extension 137. After actuator 117 is set to the eject position and is received in seat 105, as shown in FIG. 19A, filament 109 is displaced distally such that extension 137 protrudes completely from hollow needle 124. Since hook elements 138 and 139 are no longer retained by the wall of hollow needle 124, as shown in FIGS. 19B-D, extension 137 becomes detached from wire 126, allowing filament 109 to remain within container 146.

Many other means for releasing a probe into the container are within the scope of the present invention.

In FIGS. 20A-C, an oval probe 155 is fixedly connected to probe holder 156 provided with hook element 138. An actuator is fixedly attached to driving element 157 provided with hook element 139. FIG. 20A illustrates probe 155 in a partially extended position in order to be applied with a sample or when a new probe is introduced into the injector. FIG. 20B illustrates probe 155 in a retracted position The wall of hollow needle 124 retains hook elements 138 and 139 in engagement; however, when hook element 138 is displaced distally beyond needle tip 128 which has pierced membrane 144 as shown in FIG. 20C, probe holder 156 becomes detached from driving element 157.

It will be appreciated that the probe may be releasably connected to the probe holder by means of hook elements 138 and 139.

Figure 21:
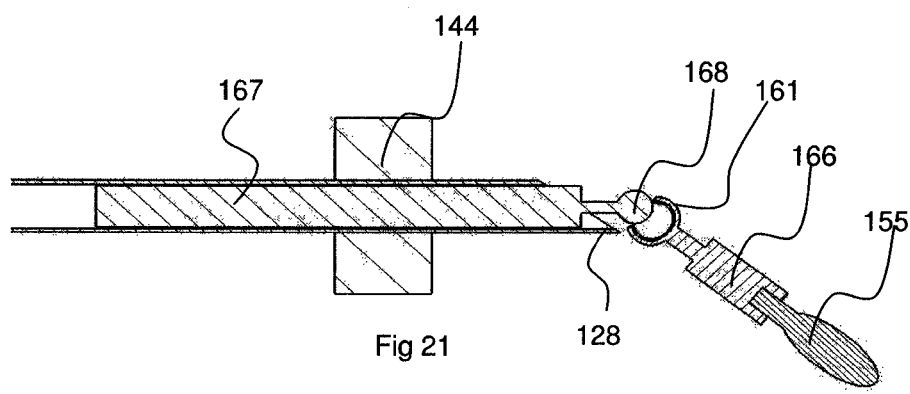
FIG. 21 is a cross sectional view of another embodiment of probe releasing means, shown in a detached position.

In FIG. 21, a concave element 161 is connected to probe holder 166. Concave element 161 is in engagement with a circular or spherical element 168 distally extending from driving element 167 until concave element 161 is displaced beyond needle tip 128 which has pierced membrane 144.

Figure 22A:
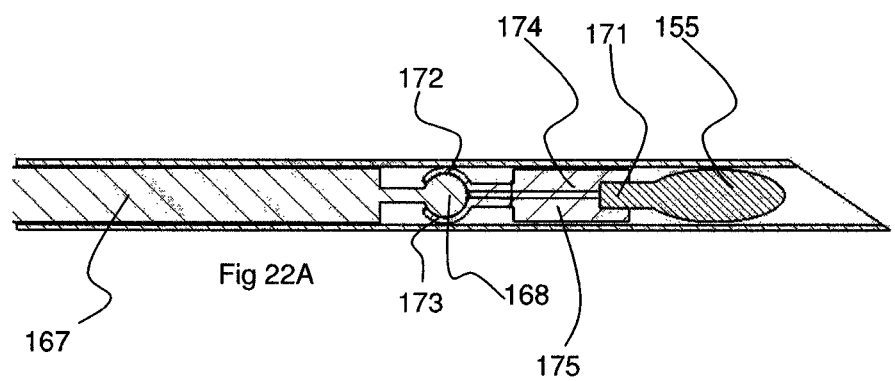
FIGS. 22A-B are cross sectional views of another embodiment of probe releasing means, shown in two different axial positions, respectively.
Figure 22B:
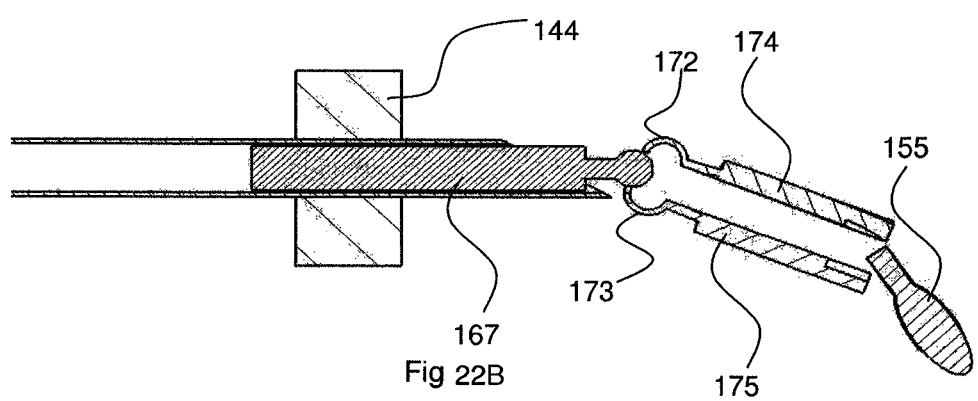

In FIGS. 22A-B, rectangular proximal element 171 of probe 155 is releasably held between two probe holder sections 174 and 175 that are separated along their entire length. Concave element sections 172 and 173 are connected to probe holder sections 174 and 175, respectively, so as to be engaged together with element 168 connected to driving element 167 until concave element sections 172 and 173 are displaced beyond needle tip 128 which has pierced membrane 144.

Figure 23:
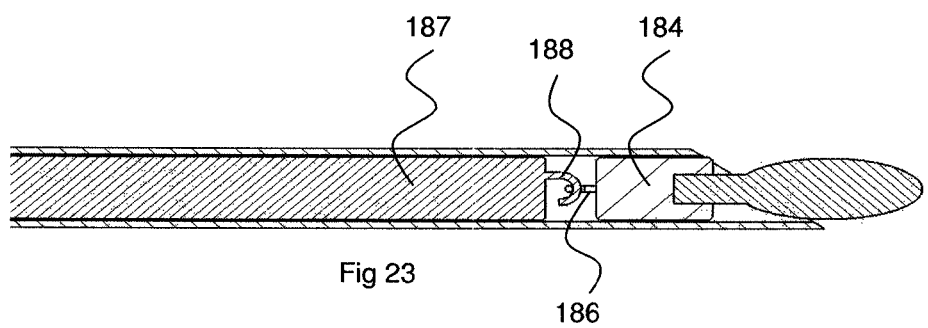
FIG. 23 is a cross sectional view of another embodiment of probe releasing means.

In FIG. 23, a straight element 186 proximally extending from probe holder is releasably engageable with an arcuate hook element 188 distally extending from driving element 187.

Figure 24A:
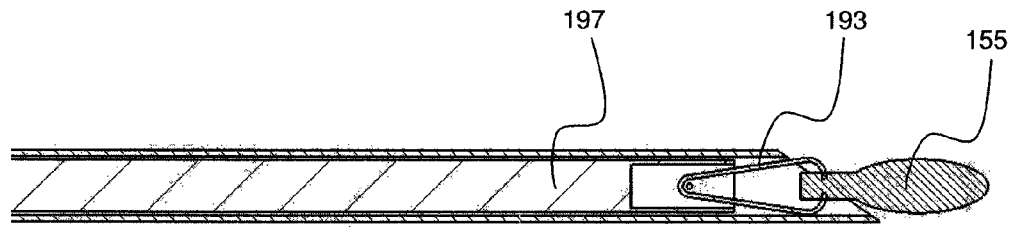
FIGS. 24A-C are cross sectional views of another embodiment of probe releasing means, shown in three different axial positions, respectively.
Figure 24B:
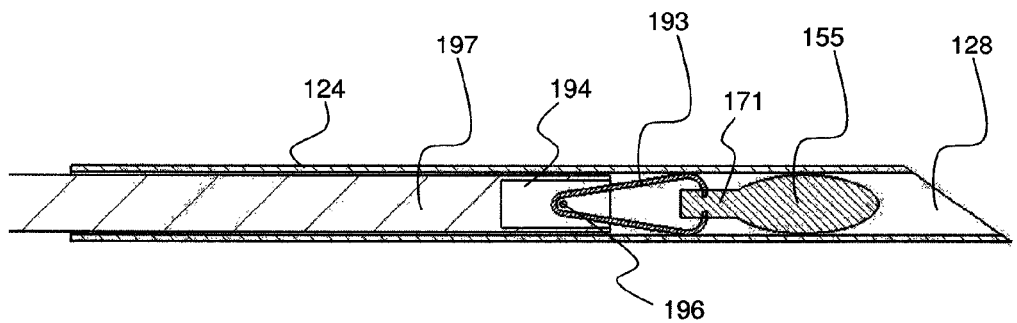
Figure 24C:
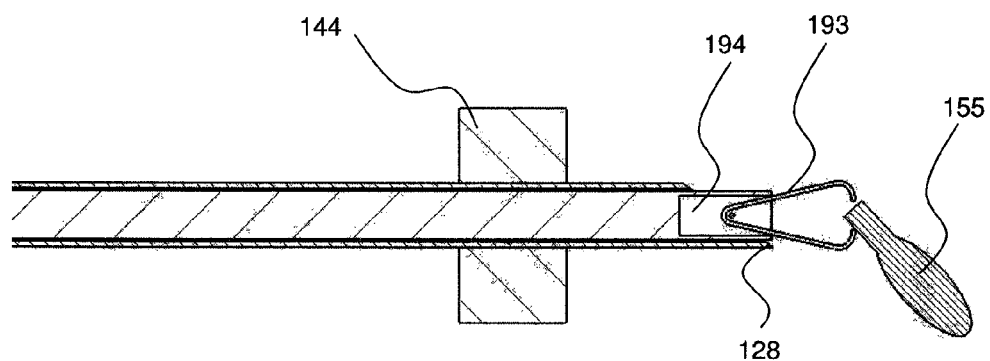

In FIGS. 24A-C, rectangular proximal element 171 of probe 155 is grasped by tong member 193 serving as the probe holder. The narrow end of probe 155 is pivotally engaged by pin 196 positioned within mounting element 194. The wall of hollow needle 124 retains probe 155 and tong member 193 in engagement therewith. When driving element 197 which is provided at its distal end with mounting element 194 is displaced until tong member 193 is distally separated from needle tip 128 which has pierced membrane 144, tong member 193 opens to release probe 155.

Figure 25A:
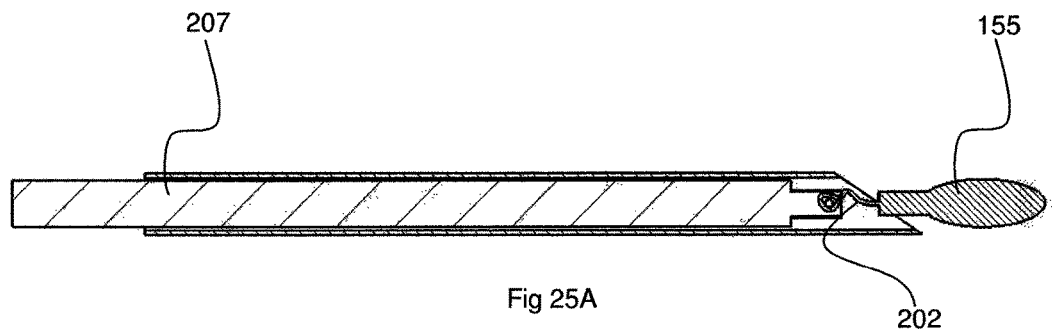
FIGS. 25A-D are cross sectional views of another embodiment of probe releasing means, shown in four different axial positions, respectively.
Figure 25B:
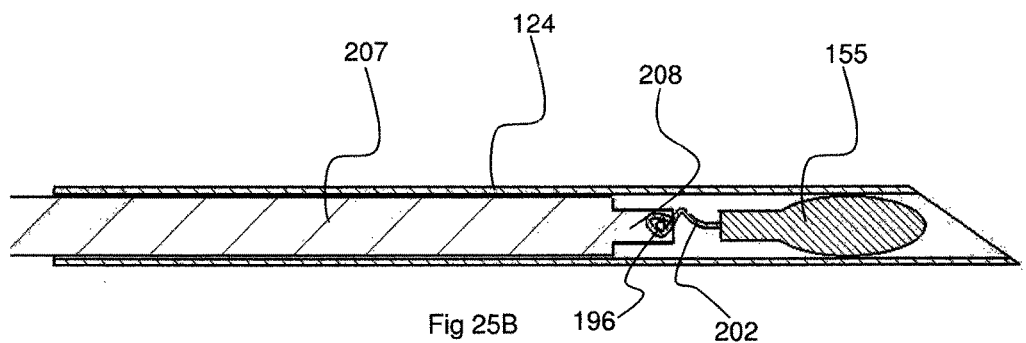
Figure 25C:
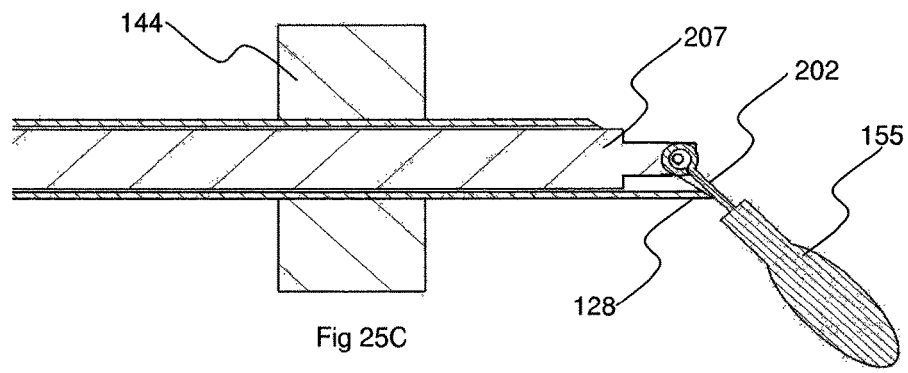
Figure 25D:
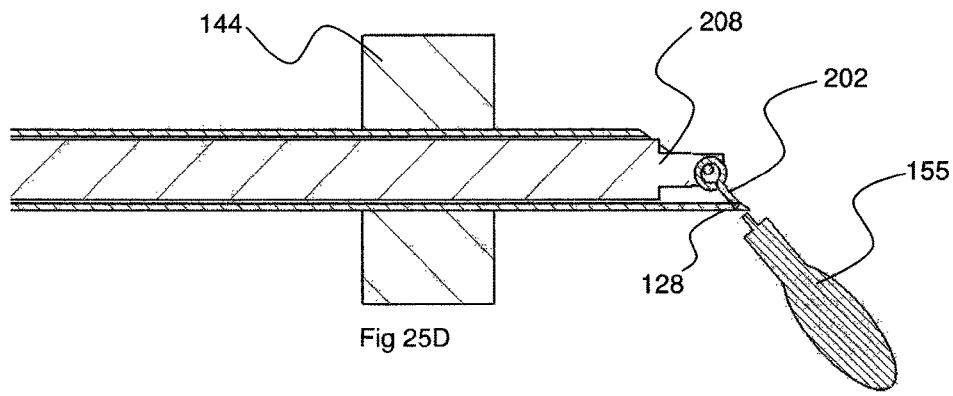

In FIGS. 25A-D, probe 155 is connected by filament 202, e.g. a weak filament that is severable upon application of a moderate amount of tensile force, to pin 196 which is provided at the distal end 208 of driving element 207. When probe 155 is located within the interior of hollow needle 124, filament 202 is slack as shown in FIG. 25B. Filament 202 becomes tensioned when the actuator connected to driving element 207 is set to the eject position and driving element 207 is displaced distally such that probe 155 is ejected into the sealed container as shown in FIG. 25C. Upon further retraction of actuator 117 as shown in FIG. 25D, probe 155 is generally unable to be returned into the interior of needle 124, causing filament 202 to become torn due to the excessive tensile force applied thereto.

Figure 26A:
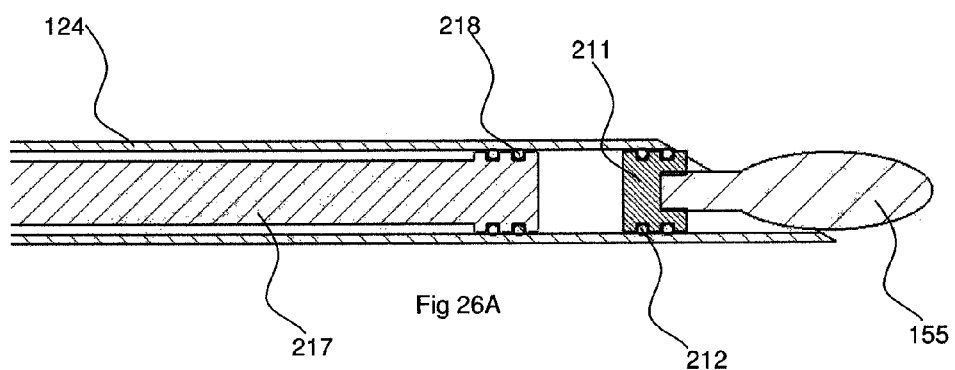
FIGS. 26A-C are cross sectional views of another embodiment of probe releasing means, shown in three different axial positions, respectively.
Figure 26B:
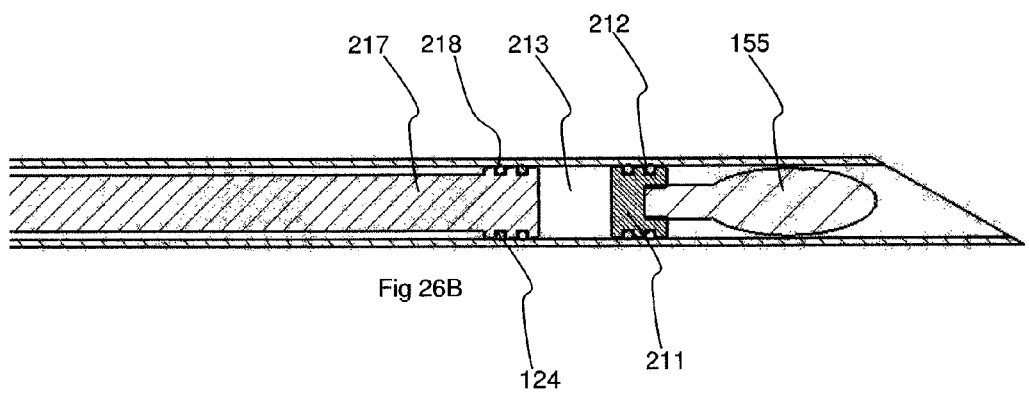
Figure 26C:
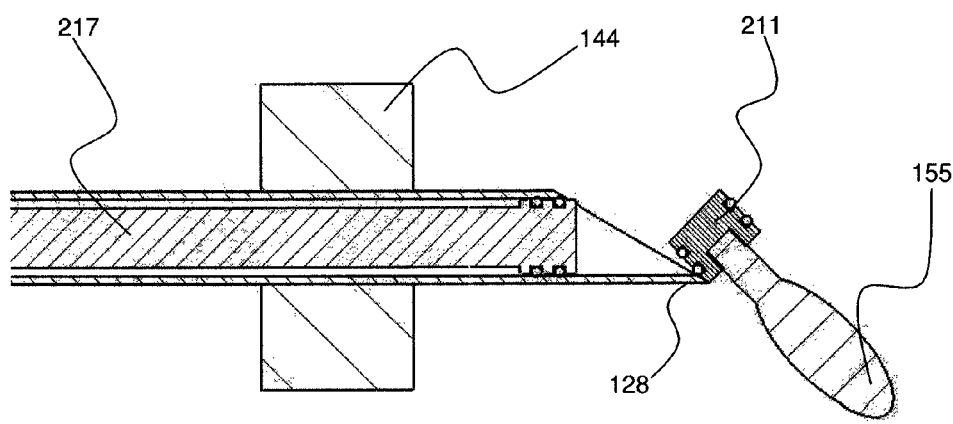

In FIGS. 26A-C, probe 155 is fixedly connected to a probe holder 211 which is engaged by seal elements 212 with the wall of hollow needle 124. A piston member 217 is also engaged with the wall of hollow needle 124 by seal elements 218. When piston member 217 is retracted proximally by means of the actuator, subatmospheric pressure is generated within needle interior 213, causing probe holder 211 to be also displaced proximally. When piston member 217 is distally displaced, the air with interior 213 becomes pressurized, causing probe holder 211 together with probe 155 to be discharged from needle tip 128.

Figure 27:
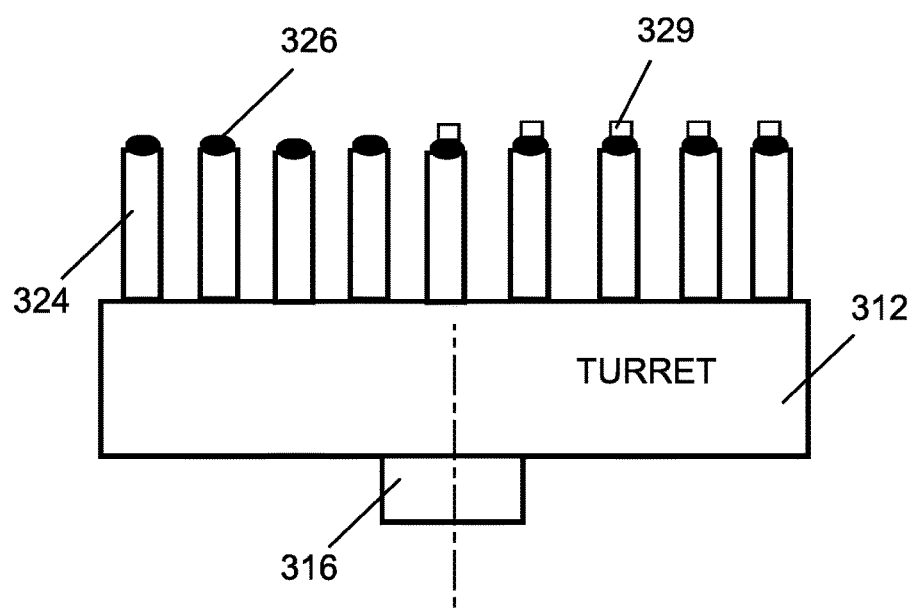
FIG. 27 is a schematic side view of an indexing turret assembly, showing some probe holders thereof from which a corresponding probe has been detached.

In another embodiment of the invention shown in FIG. 27, the injector may comprise a plurality of probes 329. A plurality of probe holders 324 which are releasably attached to corresponding probes 329 by a detachment unit 326 according to any embodiment described herein are mounted in an indexing turret assembly 312. Upon completion of a sample transfer operation to a culture bottle or any other sealed container, the turret assembly 312 is indexed by indexing mechanism 316 so that a new probe will be made accessible.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. A sterile sample injector for collecting a sample and injecting the same into a sealed container, comprising:
    a) an injector body having an axially extending cavity;
    b) a hollow needle with a pointed end which is positionable at a distal end of said injector and configured to pierce a seal of a container;
    c) a probe and a probe holder which are connected to each other, said probe holder and said probe being receivable within said hollow needle;
    d) a driving element which is axially displaceable within said axially extending cavity, for causing relative motion between said probe and said hollow needle upon axial displacement of said driving element;
    wherein said probe is selectively extendable from and retractable into said hollow needle;
    wherein the injector is configured such that at least said probe is irreversibly ejectable into the container; and
    wherein the probe is detachably connected to the probe holder by a weak engagement force such that the probe detaches from the probe holder when the probe holder retracts through the seal of the container.

2. The injector according to claim 1, wherein:
    wherein the probe, which is retractable into hollow needle:

comprises one or more absorbent or porous filaments;
is made of absorbable or porous material; or
the probe is made of compressible material such to be retractable into the hollow needle and expandable to a thickness greater than the outer diameter of the needle when extending from the hollow needle.

3. The injector according to claim 1, further comprising a manual actuator that is connected to said needle or to the driving element,
wherein the manual actuator is a pin extending into an angled groove formed in a central peripheral portion of the injector body, said pin being guidable within said groove to define a desired axial position of the probe relative to the hollow needle.

4. The injector according to claim 1, wherein the probe is detachably connectable to the probe holder or to an extension thereof by means selected from a group comprising: two interengageable hook elements, a concave element in releasable engagement with a circular or spherical element, a tong member, a straight element in releasable engageable with an arcuate hook element, a filament detachably connected to a pin, or by an adhesive.

5. The injector according to claim 1, wherein the injector body is a hollow cylinder and the driving element is a piston which is axially displaceable within said cylinder, wherein one of the hollow needle and probe holder is attached to said cylinder and one of the hollow needle and probe holder is attached to said piston to cause relative motion between the probe and the needle upon axial displacement of said piston.

6. The injector according to claim 5, wherein the probe holder is attached to a distal end of the piston, the hollow needle is attached to the cylinder, and the pin radially extends from the piston through the groove; or the hollow needle is attached to a distal end of the piston, the probe holder is attached to the cylinder, and the pin radially extends from the hollow needle through the groove.

7. The injector according to claim 1, wherein a protuberance protruding from the probe holder is releasably connected to walls of a complementary cavity formed in the probe or wherein a protuberance protruding from the probe is releasably connected to walls of a complementary cavity formed in the probe holder.

8. The injector according to claim 1, further comprising a needle related safety device.

9. The injector according to claim 4, wherein each of the two interengeageable hook elements comprises a thin element and a terminal element perpendicularly extending from said thin element and arranged such that the thin element of a first hook element is maintained in abutting relation with the terminal element of a second element by a wall of the hollow needle.

10. The injector according to claim 1, further comprising an indexing turret assembly in which a plurality of probe holders are mounted, to each of said plurality of probe holders is releasably connected a corresponding probe, wherein said turret assembly is indexable following detachment of a first probe from a first probe holder so that a second probe which is uncontaminated will be made accessible to another sample.

11. The injector according to claim 1, further comprising a needle cover which is releasably engageable with the injector body.

12. The injector according to claim 1, wherein the sample with which the probe is applicable comprises one or more of the following:
a) biological sample;
b) a non-liquid bodily extract;
c) a solid bodily extract;
d) a liquid bodily extract;
e) a biological sample usable for microbiological analysis, for genetic testing, for DNA analysis, for RNA analysis, for protein analysis, or for any biochemical testing;
f) a biological sample which is a substance that is added to another sample being stored in a sealed container;
g) a solid sample;
h) a powder;
i) a fluid sample; and
j) beads.

13. The injector according to claim 1, wherein the probe is detachable from the probe holder so that the probe is injectable into the interior of said culture bottle by means of the needle and such that the sample with the probe is accessible for microbiological analysis of the sample within said culture bottle.

14. The injector according to claim 1, further comprising a first extension connected to the driving element and a second extension connected to the probe holder.

15. The injector according to claim 1, wherein the probe is detachably connected to the probe holder such that an engagement force between the probe and the probe holder is weakened when the probe and the probe holder are in the extended position compared to the engagement force therebetween when the probe and probe holder are in the retracted position.

16. The injector according to claim 1, wherein the probe is detachably connected to the probe holder by a filament, causing said filament to be torn when the probe holder retracts through the seal.

17. The injector according to claim 1, wherein the probe is fixedly coupled to the probe holder for discharging the probe holder together with the probe from the hollow needle.

18. The injector according to claim 1, wherein the hollow needle is configured such that a puncture hole formed thereby in a seal of the sealed container will close after the needle is removed from the container.

* * * * *